United States Patent
Xiu

(10) Patent No.: US 6,399,116 B1
(45) Date of Patent: Jun. 4, 2002

(54) RHODIOLA AND USED THEREOF

(76) Inventor: Rulin Xiu, 2010 Kalorama Rd., NW., Suite 44, Washington, DC (US) 20009

(*) Notice: Subject to any disclaimer, the term of this patent is extended or adjusted under 35 U.S.C. 154(b) by 0 days.

(21) Appl. No.: 09/559,830

(22) Filed: Apr. 28, 2000

(51) Int. Cl.⁷ .............................................. A61K 35/78
(52) U.S. Cl. ...................................... 424/773; 424/725
(58) Field of Search ................................ 424/725, 773

(56) References Cited

FOREIGN PATENT DOCUMENTS

CN        1138984      *  1/1997

OTHER PUBLICATIONS

Yu et al. Planta Med. vol. 59, No. 1, pp. 80–82, 1993.*
Chen et al. Chem. Ind. Forest Prod. vol. 16, No. 1, pp. 69–74, 1996.*
Peng et al. Nat. Med. vol. 50, No. 5, pp. 358–362, 1996.*
List of Herbs Extract Powder, 1 page, from huayitcm.com website, 2001.*
Du et al. Huaxue Xuebao. vol. 52, No. 9, pp. 927–931, abstract enclosed, 1994.*
Peng et al. Zhongcaoyao. vol. 26, No. 4, pp. 177–179, abstract enclosed, 1995.*
Wang et al. Yaoxue Xuebao. vol. 27, No. 2, pp. 117–120, abstract enclosed, 1992.*
Peng et al. Yaowu Fenxi Zazhi. vol. 15, No. 4, pp. 21–23, abstract enclosed, 1995.*
Natural Products Industry Insider, 6 pages, from natural-productsinsider.com website, pp. 4–5, Mar. 2001.
Article titled Rhodiola, 3 pages, from SupplementWatch.com website, 2001.
Article titled Dragon Herbs, 4 pages, from dragonherbs.com website, 2001.
Raw Materials Listing, 2 pages, from gmaherbs.com website, 2001.

* cited by examiner

*Primary Examiner*—Christopher R. Tate
(74) *Attorney, Agent, or Firm*—Millen, White, Zelano & Branigan, P.C.

(57) ABSTRACT

The present invention relates to Rhodiola, preferably *Rhodiola crenulata,* to treat various conditions and diseases in mammals. *Rhodiola crenulata* is a Tibetan herb which has been discovered to have highly useful and beneficial properties heretofore unknown. *Rhodiola crenulata* is especially preferred to enhance blood oxygen levels, to enhance working capacity and endurance, to enhance memory and concentration, to enhance cardiac and cardiovascular function, to provide antioxidant effects, to protect against oxidation, to modulate testosterone and estradiol levels, to modulate sleep, and to enhance sexuability, such as improve sexual performance.

5 Claims, No Drawings

RHODIOLA AND USED THEREOF

DETAILED DESCRIPTION OF THE INVENTION

The present invention relates to compositions, articles of manufacture, extracts, compounds, methods of use, methods of treatment, methods of preparation, etc., which relate to plants of the genus Rhodiola, preferably *Rhodiola crenulata*, which have a variety of useful and beneficial effects, including, e.g., to enhance blood oxygen and nutrients levels, e.g., through enhancing oxygen transport, to enhance working capacity and endurance, to reduce muscle fatigue, to enhance memory and concentration, to reduce stress, to enhance cardiac and cardiovascular function, to provide antioxidant effects, to protect against oxidation, to provide anti-cancer effects, to promote DNA repair, to provide anti-radiation effects, to protect against radiation, to reduce inflammation, to increase insulin, to decrease levels of glucagon, to reduce histamine release, to reduce allergic reactions, preferably, to modulate testosterone levels, and to modulate sleep, especially to promote sleep, to modulate blood lipids, preferably, e.g., to lower cholesterol levels, to promote weight loss, and to enhance sexuability, such as improve sexual performance.

*Rhodiola crenulata* is a species of Rhodiola which grows mostly in Tibet and south west of China on the altitude between 3400 meters to 5600 meters. It has been used in Tibetan medicine for more than 1000 years for uses that have been limited to curing lung inflammation and cough, for stopping and activating blood, and for treating external wounds and burns. It has been discovered herein that *Rhodiola crenulata* has other beneficial properties that make it useful for a variety of conditions and diseases, as mentioned above and below.

Rhodiola is a diverse genus of plants which includes more than 50 different species, including, e.g., *algida, arctica, crenulata, elongata, gelida, imbricataishidae, iremelica, kirilowii, linearifolia, phariensis, pinnatifida, quadrifida,* aff. *quadrifida, rosea, sachalinensis,* and *wolongensis*. These species vary from each other widely, differing in, e.g., chromosome number (e.g., Makoto et al., *Journal of Japanese Botany*, 70(6):334–338, 1995), chemical composition, morphology, medicinal properties, developmental stages (e.g., Ishmuratatova and Satsyperova, *Rastitel'nye Resursy.*, 34(1):3–11, 1998), geographical distribution, etc. Scientific studies (e.g. Peng et al, *Chinese Herb Medicine* (1995), 26(4): 177–179, and Wang et al, *Acta Phrmaceutica Sinica* (1992), 27(2): 117–120) indicate constituents of *Rhodiola crenulata* include, e.g., salidroside, tyrosol, β-sitosterol, gallic acid, pyrogallol, crentulatin, rhodionin, rhodiosin, among which, crenulatin, e.g., is found only in *R. crenulata* and has not been found in any other Rhodiola species. Rhodiosin and rhodionin exists in some, but not all, Rhodiola species.

The term "plant" as used herein refers to seeds, leaves, stems, flowers, roots, berries, bark, or any other plant parts that are useful for the purposes described. For certain uses, it is preferred that the underground portion of the plant, such as the root and rhizoma, be utilized. The leaves, stems, seeds, flowers, berries, bark, or other plant parts, also have medicinal effects and can be used for preparing tea and other beverages, cream, and in food preparation.

Rhodiola of the present invention can be in any form which is effective, including, but not limited to dry powders, grounds, emulsions, extracts, and other conventional compositions. To extract or concentrate the effective ingredients of Rhodiola, typically the plant part is contacted with a suitable solvent, such as water, alcohol, methanol, or any other solvents, or mixed solvents. The choice of the solvent can be made routinely, e.g., based on the properties of the active ingredient that is to be extracted or concentrated by the solvent. Preferred active ingredients of *Rhodiola crenulata* include, but are not limited to, salidroside, tyrosol, β-sitosterol, gallic acid, pyrogallol, crenulatin, rhodionin, and/or rhodiosin. These ingredients can be extracted in the same step, e.g., using an alcoholic solvent, or they may be extracted individually, each time using a solvent which is especially effective for extracting the particular target ingredient from the plant. In certain embodiments, extraction can be performed by the following process: Milling the selected part, preferably root, to powder. The powder can be soaked in a desired solvent for an amount of time effective to extract the active agents from the Rhodiola. The solution can be filtered and concentrated to produce a paste that contains a high concentration of the constituents extracted by the solvent. In some cases, the paste can be dried to produce a powder extract of *Rhodiola crenulata*. The content of active ingredient in the extract can be measured using HPLC, UV and other spectrometry methods.

A Rhodiola of the present invention can be administered in any form by any effective route, including, e.g., oral, parenteral, enteral, intraperitoneal, topical, transdermal (e.g., using any standard patch), ophthalmic, nasally, local, non-oral, such as aerosal, inhalation, subcutaneous, intramuscular, buccal, sublingual, rectal, vaginal, intra-arterial, and intrathecal, etc. It can be administered alone, or in combination with any ingredient(s), active or inactive, including in a medicinal form, or as a food or beverage additive.

In preferred embodiments of the invention, Rhodiola is administered orally in any suitable form, including, e.g., whole plant, powdered or pulverized plant material, extract, pill, capsule, granule, tablet or a suspension.

Rhodiola can be combined with any pharmaceutically acceptable carrier. By the phrase, "pharmaceutically acceptable carriers," it is meant any pharmaceutical carrier, such as the standard carriers described, e.g., *Remington's Pharmaceutical Science*, Eighteenth Edition, Mack Publishing company, 1990. Examples of suitable carriers are well known in the art and can include, but are not limited to, any of the standard pharmaceutical carriers such as a phosphate buffered saline solutions, phosphate buffered saline containing Polysorb 80, water, emulsions such as oil/water emulsion and various type of wetting agents. Other carriers may also include sterile solutions, tablets, coated tablets pharmaceutical and capsules. Typically such carriers contain excipients such as such as starch, milk, sugar, certain types of clay, gelatin, stearic acid or salts thereof, magnesium or calcium stearate, talc, vegetable fats or oils, gums, glycols. Such carriers can also include flavor and color additives or other ingredients. Compositions comprising such carriers are formulated by well known conventional methods. Generally excipients formulated with Rhodiola are suitable for oral administration and do not deleteriously react with it, or other active components.

Suitable pharmaceutically acceptable carriers include but are not limited to water, salt solutions, alcohols, gum arabic, vegetable oils, benzyl alcohols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose and the like. Other additives include, e.g., antioxidants and preservatives, coloring, flavoring and diluting agents, emulsifying and suspending agents, such as acacia, agar, alginic acid, sodium alginate, bentonite, carbomer, carrageenan, carboxymethylcellulose, cellulose, cholesterol, gelatin, hydroxyethyl cellulose, hydroxppropyl cellulose, hydroxypropyl methylcellulose, methylcellulose, octoxynol 9, oleyl alcohol, povidone, propylene glycol monostearate, sodium lauryl sulfate, sorbitan esters, stearyl alcohol, tragacanth, xanthan gum, and derivatives thereof, solvents, and miscellaneous ingredients such as microcrystalline cellulose, citric acid, dextrin, dextrose, liquid glucose, lactic acid, lactose, magnesium chloride, potassium metaphosphate, starch, and the like.

Rhodiola can also be formulated with other active ingredients, such as anti-oxidants, vitamins (A, C, ascorbic acid, B's, such as B1, thiamine, B6, pyridoxine, B complex, biotin, choline, nicotinic acid, pantothenic acid, B12, cyanocobalamin, and/or B2, D, D2, D3, calciferol, E, such as tocopherol, riboflavin, K, K1, K2). Preferred compounds, include, e.g creatine monohydrate, pyruvate, L-Carnitine, α-lipoic acid, Phytin or Phytic acid, Co Enzyme Q10, NADH, NAD, D-ribose, amino acids such as L-Glutamine, Lysine, chrysin; pre-hormones such as 4-drostenedione, 5-androstenedione, 4(or 5-)androstenediol, 19-nor-4 (or 5-)-drostenedione, 19-nor-4 (or 5-)-androstenediol, Beta-ecdysterone, and 5-Methyl-7-Methoxy Isoflavone. Preferred active ingredients include, e.g., pine pollen, fructus lycii, hippophae rhamnoides, Salvia Miltiorrhiza, Ligusticum, Acanthopanax, Astragalus, Ephedra, codonopsis, polygola tenuifolia Willd, Lilium, Sparganium, ginseng, panax notogiseng, Garcinia, Guggle, Grape Seed Extract or powder, and/or Ginkgo Biloba.

Other plants and herbs which can be formulated with a Rhodiola of the present invention includes those mentioned in various text and publications, e.g., *ES Ayensu, Medicinal Plants of West Africa,* Reference Publications, Algonac, Mich. (1978); P. Back, *The Illustrated Herbal* 1987, Hamlyn Publishers, distributed by Octopus Books, Printed in Hong Kong by Mandarin, ISBN 0-600 553 361; F. Bianchini and F. Corbetta, *The Fruits of the Earth,* translated from Italian by A. Mancinelli, Bloomsbury Books, London, ISBN 1-870630-10-6; H. M. Burkill, *The Useful plants of West Tropical Africa,* Ed. 2, V. I, Royal Botanic Gardens Kew, ISBN 0-947643-01-X (1985); L. Boulos, *Medicinal Plants of North Africa,* Reference Publications Inc., Algonac, Mich. (1983); and N. C. Shah, *Herbal Folk Medicines in Northern India,* J. Ethnopharm, 6:294–295 (1982).

Other active agents include, e.g., antioxidants, anticarcinogens, anti-inflammatory agents, hormones and hormone antagonists, antibiotics (e.g., amoxicillin) and other bacterial agents, and other medically useful drugs such as those identified in, e.g., *Remington's Pharmaceutical Sciences,* Eighteenth Edition, Mack Publishing Company, 1990. A preferred composition of the present invention comprises, about 1%–100%, preferably about 20–70% *Rhodiola crenulata* extract, more preferably about 60%, said extract having about 0.5–10% salidroside content; 10–45% 5:1 extracted fructus lycii powder (5 kilograms of the herb is used to produce 1 kg of herb powder); 1–20% of hippophae rhamnoides powder; and, optionally, a pharmaceutically-acceptable excipient.

The present invention relates to methods of administering Rhodiola, especially *Rhodiola crenulata,* e.g., to enhance blood oxygen levels, to enhance working capacity and endurance, to reduce muscle fatigue, to enhance memory and concentration, to reduce stress, to enhance cardiac and cardiovascular function, to improve sexual ability, to provide antioxidant effects, to protect against oxidation, to provide anti-cancer effects, to promote DNA repair, to provide anti-radiation effects, to protect against radiation, to reduce inflammation, to increase insulin, to decrease levels of glucagon, to reduce histamine release, to reduce allergic reactions, preferably, to modulate testosterone levels, to increase male virality, to modulate sleep, especially to promote sleep. to modulate blood lipids, preferably, e.g., to lower cholesterol levels, to promote weight loss, to increase estradiol levels, etc., and other conditions and diseases as mentioned above and below.

By the term "administering," it is meant that Rhodiola is delivered to the host in such a manner that it can achieve the desired purpose. As mentioned Rhodiola can be administered by an effective route, such as orally, topically, rectally, etc. Rhodiola can be administered to any host in need of treatment, e.g., vertebrates, such as mammals, including humans, male humans, female humans, primates, pets, such as cats and dogs, livestock, such as cows, horses, birds, chickens, etc.

An effective amount of Rhodiola is administered to such a host. Effective amounts are such amounts which are useful to achieve the desired effect, preferably a beneficial or therapeutic effect as described above. Such amount can be determined routinely, e.g., by performing a dose-response experiment in which varying doses are administered to cells, tissues, animal models (such as rats or mice in maze-testing, swimming tests, toxicity tests, memory tests as performed by standard psychological testing, etc.) to determine an effective amount in achieving an effect. Amounts are selected based on various factors, including the milieu to which the virus is administered (e.g., a patient with cancer, animal model, tissue culture cells, etc.), the site of the cells to be treated, the age, health, gender, and weight of a patient or animal to be treated, etc. Useful amounts include, 10 milligrams-100 grams, preferably, e.g., 100 milligrams-10 grams, 250 milligrams-2.5 grams, 1 gm, 2 gm, 3 gm, 500 milligrams-1.25 grams. etc., per dosage of different forms of *Rhodiola crenulata* such as the herbal powder, herbal extract paste or powder, tea and beverages prepared to contain the effective ingredients of Rhodiola, injections, depending upon the need of the recipients and the method of preparation.

In preferred embodiments, the present invention relates to a method of increasing testosterone levels in a host in need thereof, comprising, administering an effective amount of a Rhodiola to said host. Testosterone, principal male hormone, or androgen, is produced mainly in the Leydig cells in the male testes. The Leydig cells also produce two other androgens of less potency and in much smaller quantities. Testosterone stimulates the development of the male secondary sex characteristics after puberty, causing growth of the beard and pubic hair, development of the penis, and change of voice. The hormone also aids in growth, muscular development, and masculine body contour of the adult male.

Testosterone is considered to be a male virilizing hormone. Its effects include maintenance of muscle and bone mass, improving and/or enhancing sexual function and psychological well being among others. As males grow older, especially after the age of 35, a slow decline in testosterone levels is observed which is accompanied by symptoms that have been associated with the condition known as "andropause". Symptoms of andropause include lethargy, depression, lack of sexual desire and function, and loss of muscle mass and strength. Increasing testosterone levels therefore can be useful to treat any of the mentioned conditions. Additionally, increasing testosterone levels can be useful in treating certain types of breast cancer in women.

Testosterone levels refer to the amounts of testosterone which are circulating in the blood, e.g., as measured using enzyme-linked immunosorbent assay, HPLC, or any other suitable detection method.

Any effective amount of *Rhodiola crenulata* can be administered. In accordance with present invention, it has been demonstrated that intake of a standardized *Rhodiola crenulata* extract (e.g., having 0.1–10%. Preferably 1–6%) salidroside by total weight of composition) produced a significant increase in total testosterone as compared to placebo. For example, after taking 2 grams of standardized rhodiola extract with 2% salidroside, once a day for a month, subjects showed about a 76% increase in total testosterone in the blood as compared to the 6.0% increase in total testosterone level after taking placebo for a month. These amounts, however, can be increased by any value, e.g., at least about 5%, 10%, 15%, 20%, 50%, 60% 70%, 75%, 100%, 2-fold, 5-fold, etc., over amounts which are present in the blood prior to administration.

The present invention also relates to a method of increasing estradiol levels in a host in need thereof, comprising, administering an effective amount of a Rhodiola to said host.

Estradiol is a female sex hormone that stimulates the appearance of secondary female sex characteristics in girls at puberty. Estradiol controls growth of the lining of the uterus during the first part of the menstrual cycle, cause changes in the breast during pregnancy, and regulate various metabolic processes. Increasing estradiol can treat various conditions, including menopausal symptoms, estrogen deficiencies in women (most commonly after menopause; low eight; etc) and inflammation of the vagina. It can also stimulate lactation following childbirth and in the treatment, but not cure, advanced and even disseminated cancer of the prostate gland in men. Amounts of estradiol can be increased by any value, e.g., 5%, 6%, 8%, 10%, 15%, 20%, 30%, 50%, 75%, 100%, 2-fold, 5-fold, etc., over amounts which are present in the blood prior to administration. For example, in Example 10, Rhodiola as effective in increasing estradiol levels by about 12% as compared to only 3% in controls. Thus, Rhodiola can used to treat conditions associated with estrogen deficiency, such as menopuse, perimenopause, lowweight, etc.

Rhodiola can be combined with any agent which raises testosterone and/or estradiol levels. For example, testosterone precursors, such as those disclosed in U.S. Pat. Nos. 5,880,117 and 6,011,027, e.g., 4-androstenediol and 19-nor-4-androstenediol, can be utilized in combination with Rhodiola as a means of increasing testosterone levels in human. Currently, 4-androstenedione, 5-androstenedione, 4-androstenediol, 5-androstenediol, 19-nor-4-androstenedione, 19-nor-5-androstenedione, 19-nor-4-androstenediol, and 19-nor-5-androstenediol, Beta-ecdysterone, and 5-Methyl-7-Methoxy Isoflavone are being used to increase the testosterone level in humans. *Rhodiola crenulata* can be used with these ingredients to enhance their effects of boosting the testosterone level, other hormones, such as estradiol. *Rhodiola crenulata* can also be formulated to boost hormonal levels with other herbs, such as wild yam, Epimedium (including all Epimedium species), Angelica, Lycium, panex ginseng, *Ganoderma lucidum,* Codonopsis, Eleutherococcus, *Schisandra chinensis,* Atractylodes, and *Ligustrum lucidum.*

The present invention also relates methods of improving sleep in a host in need thereof, comprising administering an effective amount of a Rhodiola to said host. By the phrase "improving sleep," it meant bringing about a beneficial effect on sleep, including, e.g., prolonging sleep time (e.g., as measured in animal models by administering Rhodiola in the presence or absence of a barbiturate, or other sleep-promoting agent, and determining the sleep-prolongation time produced by Rhodiola), increasing time spent in REM-sleep, reducing sleep apnea and other sleep disorders, decreasing insomnia, decreasing amount of time to fall asleep, etc.

Rhodiola can also be formulated with other agents which promote sleep, such as Valerian, Melatonin, Kava Kava, St. John's Wort, Tryptophan and 5-Hydroxytryptophan, Astragalus, Hops, Passionflower, Skullcap, Chamomile, He Shou Wu, Ashwaganda, and Lady's Slipper.

The present invention also relates to methods of treating impotence, comprising administering an effective amount of Rhodiola, preferable *Rhodiola crenulata.* Impotency, or erectile dysfunction, is the inability to achieve an erection. The ability of *Rhodiola crenulata* to increase the blood oxygen transportation and testosterone level can enhance male sexual ability and performance in some cases. The Rhodiola can be administered immediately prior to performance, or more preferably, on a daily basis according to the regime mentioned above to increase testosterone levels. Rhodiola can also be administered in combination with agents which are used for treating impotency, including, e.g., vasodilators, phosphodiesterase inhibitors, stimulators of NO release, alpha-adrenergic agents, etc.

Administration of *Rhodiola crenulata* can also be used to enhance blood oxygen levels and transport to body tissues; to enhance working capacity and endurance. By "working capacity and endurance," it preferably meant that the effective amount increases the ability to perform a physical task, such as in exercise, physical labor, or sports activity, even before fatigue would normally occur; thus, enhanced working capacity and endurance is defined herein not to mean "fatigue," which simply indicates that the performer does not tire. Associated with enhanced working capacity and endurance can be an increase in muscle ATP levels and a reduction in circulating lactic acid levels (see, Examples 2 and 3). Thus, the present invention also relates to methods of increasing muscle ATP levels and/or reducing lactic acid in blood, thereby enhancing working capacity and endurance, improving sexual performance, etc.

As shown in the Example 2, *Rhodiola crenulata* reduces blood lactic acid (lactate) levels. Such reduction in lactic acid levels indicates that muscle fatigue is reduced. By "muscle fatigue," it is meant that the muscle cells carry out anaerobic respiration because of lack of oxygen. Reducing muscle fatigue therefore means, e.g., that fewer muscle cells become anaerobic. The present invention therefore also relates to a method of reducing muscle fatigue comprising administering an effective amount of *Rhodiola crenulata.* Lactic acid can be reduced by an effective amount in ameliorating fatigue, such as at least 10%, 15%, 20%, 25%, 30%, 35%, etc.

As shown in Example 3, *Rhodiola crenulata* increases the ATP available to muscle, e.g., by increasing aerobic respiration, by increasing oxygen transport, etc. Amounts of ATP can be increased by an effective amount in reducing muscle fatigue, such as 20%, 25%, 30%, 35%, 37%, 40%, 40%, 45%, 50%, etc.

Rhodiola can also be used to enhance or improved memory and concentration (such improved functions are to be distinguished from the more general brain stimulation which indicates increased non-selective neuronal activity, whereas the mentioned improved functions are selective, e.g., by stimulating specific parts of the brain or other organs, or by stimulating specific neural and hormonal systems); to reduce stress, e.g., lower blood pressure, reduce anxiety, promote calmness; to enhance cardiac and cardiovascular function (including, e.g., to protect against heart disease); to provide antioxidant effects and protect against oxidation; to provide anti-cancer effects, e.g., promote cessation of cell growth; to promote DNA repair; to provide anti-radiation effects and to protect against radiation, e.g., as a sun-screen when applied topically to the skin; to reduce inflammation, e.g., systemic inflammation, skin inflammation (where Rhodiola can be administered topically), but with the proviso that it is not lung-inflammation, coughing, or bleeding associated with lung-inflammation and coughing, to increase insulin, to decrease levels of glucagon, to reduce histamine release, to reduce allergic reactions, to enhance sexual ability. *Rhodiola crenulata* in accordance with the present invention is preferably not used to treat external wounds, external burns, lung inflammation, and coughing.

EXAMPLES

Method of Examples One, Two, and Three

20 Kunming-species mice (10 males and 10 females), weighing approximately 18–22 grams each, were randomly divided into experimental and control groups, with each group containing 10 mice. Mice in the experimental group were provided with food containing about 50 mg (0.05 gram, about 0.25 gram every 1 kilogram body weight) *Rhodiola crenulata* per day for 3 days. Mice in the control group were fed with the same food but without *Rhodiola crenulata*.

Example One

After 3 days of consuming food containing *Rhodiola crenulata*, the mice were subjected to a swimming test. A lead weight that comprised about 6% of the mice's body weight was attached to each mouse prior to placing it in a water-filled receptacle. The average survival time for experimental group was $92.85 \pm 5.20$ minutes while for the control group it was $69.89 \pm 5.10$ minutes. This represents a 33% improvement in the endurance of mice fed *Rhodiola crenulata* as compared to controls.

Example Two

After one hour of swimming, the blood lactate levels were assayed as a measure of fatigue. The average blood lactate level for the experimental group was $14.50 \pm 1.41$ mmol/L while the control group was $19.30 \pm 1.80$ mmol/L. Thus, muscle fatigue levels were reduced by 25% in mice fed *Rhodiola crenulata*.

Example Three

After one hour of swimming, the levels of skeletal muscle ATP level were measured. The average skeletal ATP level for the experimental group was $210.45 \pm 14.88$ mg/100 g while for the control group it was $153.88 \pm 20.67$ mg/100 g. ATP levels were increased by 37% in mice fed *Rhodiola crenulata*, indicating that the herb enhanced energy levels.

Method for Example Four, Five, Six, Seven, Eight, Nine, Ten, Eleven 40 volunteers are divided into two groups, each comprising 20 people. The test group was administered 2 grams of *Rhodiola crenulata* standardized extract (with 2% salidroside), once a day for one month. The control group received a placebo. After one month, each participant was required to assess improvement of their memory, sleep, physical strength, and sexual performance. Blood samples were collected prior to taking any Rhodiola and after the one-month period.

Example Four

Using a blood oxygen analyzer, the blood oxygen pressure of each participant before and after taking rhodiola crenulata extract and placebo was tested. The average of the blood oxygen pressure of the test group before and after taking rhodiola crenulata for a month was $6.97 \pm 0.64$ and $7.86 \pm 0.90$ respectively. For the control group, the average testosterone level before and after taking placebo for a month was $6.87 \pm 0.66$ and is $7.04 \pm 0.95$ respectively. These results show after taking *Rhodiola crenulata* for one month, the oxygen transport and supply in the human body is enhanced by about 12.6%.

Example Five

The test subjects were asked whether their memory was improved during the course of the test. In the test group, 45% stated that their memory was improved after one month of the medication. In the control group, only 21% reported memory improvement after one month of the placebo.

Example Six

The test subjects were asked whether their physical strength was improved. In the test group, 81% reported improvements in physical strength after one month of the medication as compared to only 38% in the control group.

Example Seven

Test subjects were asked whether their sexual performance was improved. In the test group, 75% described improved sexual performance after one month of the Rhodiola extract. In the control group, only 28.9% said their sexual performance was improved.

Example Eight

Test subjects were asked whether their sleep is improved. In the test group, 83% of the subjects their sleep was improved after one month of the Rhodiola. In the control group, 41% said their sleep is improved after one month medication.

Example Nine

Using an enzyme-linked immunosorbent assay, the blood testosterone levels of each participant was tested. The average of testosterone level of the test group before and after taking *Rhodiola crenulata*, once a day, for a month was $17.68 \pm 5.6$ mmol/L and $31.12 \pm 10.6$ mmol/L, respectively. For the control group, the average testosterone level before and after taking placebo for a month was $18.02 \pm 6.0$ mmol/L and $19.10 \pm 7.6$ mmol/L respectively. The Rhodiola increased testosterone levels by 76%, while in controls the increase was only 6%.

Example Ten

Using an enzyme-linked immunosorbent assay, the blood estradiol levels of each participant before and after taking rhodiola crenulata extract and placebo were tested. The average of estradiol level of the test group before and after taking *Rhodiola crenulata* for a month was $163.56 \pm 33.9$ mmol/L and $182.93 \pm 107.34$ mmol/L respectively. For the control group, the average estradiol level before and after taking placebo for a month was 164.5±34.43 mmol/L and 169.30±40.02 mmol/L respectively. Rhodiola increased estradiol levels by about 12% whereas in control the increase was only about 3%.

Example Eleven

The blood content of superoxide dismutase (SOD) levels of each participant was tested using the method of pyrogallol auto-oxidization before and after taking *Rhodiola crenulata* extract and placebo. The average of SOD level of the test group before and after taking *Rhodiola crenulata* for a month was 1173.8±122.2 U/g.Hb and 1296.7±157.3 U/g.Hb respectively. For the comparison group, the average testosterone level before and after taking placebo for a month was 1173.4±121.5 U/g.Hb and 1205.8±147.40 U/g.Hb respectively. This test indicates that *Rhodiola crenulata* has antioxidant effects.

Example Twelve

A composition comprising effective amounts of *Rhodiola crenulata* can be administered to subjects to enhance levels of blood oxygen, to enhance working capacity and endurance, to enhance memory and concentration, to reduce stress, to enhance cardiac and cardiovascular function, to provide antioxidant effects, to modulate testosterone levels, to modulate sleep, and to improve sexual performance. to increase energy level, and to enhance memory and concentration. Such a composition can comprise, by weight:

60% *Rhodiola crenulata,* having 2% salidroside content; and

30% of a 5:1 extracted fructus lycii powder; and

10% of hippophae rhamnoides powder.

Without further elaboration, it is believed that one skilled in the art can, using the preceding description, utilize the present invention to its fullest extent. The preceding preferred specific embodiments are, therefore, to be construed as merely illustrative, and not limiting the remainder of the disclosure in any way whatsoever. The entire disclosure of all applications, patents and publications, cited above and in the figures are hereby incorporated by reference in their entirety.

What is claimed:

1. A method of enhancing transport of blood oxygen in a subject having muscle fatigue, comprising, administering an effective amount of a water and/or alcoholic extract obtained from the roots or rhizome of *Rhodiola crenulata* to said subject, wherein said extract contains 2–10%, by weight, of salidroside, whereby said amount of Rhodiola is effective to reduce blood levels of lactic acid.

2. A method of claim 1, wherein said amount of Rhodiola is further effective to raise skeletal muscle levels of ATP.

3. A method of claim 2, wherein the skeletal muscle levels of ATP are raised at least 30%.

4. Am method of claim 1, wherein blood levels of lactate are reduced at least 20%.

5. A method of claim 1, with the proviso that said subjects do not have lung inflammation, coughing, or an external wound or burn.

* * * * *